(12) United States Patent
Freimuth et al.

(10) Patent No.: US 8,535,908 B2
(45) Date of Patent: Sep. 17, 2013

(54) FACILITATING PROTEIN SOLUBILITY BY USE OF PEPTIDE EXTENSIONS

(75) Inventors: Paul I. Freimuth, East Setauket, NY (US); Yian-Biao Zhang, Middle Island, NY (US); Jason Howitt, London (GB)

(73) Assignee: Brookhaven Science Associates, LLC, Upton, NY (US)

( * ) Notice: Subject to any disclaimer, the term of this patent is extended or adjusted under 35 U.S.C. 154(b) by 351 days.

(21) Appl. No.: 12/684,195

(22) Filed: Jan. 8, 2010

(65) Prior Publication Data

US 2010/0144029 A1    Jun. 10, 2010

Related U.S. Application Data

(63) Continuation-in-part of application No. 10/037,243, filed on Jan. 4, 2002, now abandoned.

(51) Int. Cl.
  *C12P 21/06*    (2006.01)
  *C07H 21/04*    (2006.01)
  *C12N 5/02*    (2006.01)

(52) U.S. Cl.
  USPC ........................................ 435/69.1; 536/23.1

(58) Field of Classification Search
  None
  See application file for complete search history.

(56) References Cited

U.S. PATENT DOCUMENTS

| | | |
|---|---|---|
| 5,563,046 A | 10/1996 | Mascarenhas et al. |
| 5,989,868 A | 11/1999 | Harrison et al. |
| 6,077,689 A | 6/2000 | Snavely |
| 6,207,420 B1 | 3/2001 | Harrison et al. |
| 6,872,551 B2 | 3/2005 | Lima et al. |

OTHER PUBLICATIONS

Zhou, et al., "A solubility-enhancement tag (SET) for NMR studies of poorly behaving proteins," *J. Biomolecular NMR*, 20, 11-14 (2001).
Baneyx, F., "Recombinant protein expression in *Escherichia coli*," *Curr. Opin. Biotech.*, 10, 411-421 (1999).
Swartz, J.R., "Advances in *Escherichia coli* production of therapeutic proteins," *Curr. Opin. Biotech.* 12, 195-201 (2001).
Condron, et al., "Frameshifting in Gene 10 of Bacteriophage T7," *J. Bacteriol.*, 173, No. 21, 6998-7003 (1991).
Ford, et al., "Fusion Tails for the Recovery and Purification of Recombinant Proteins," *Protein Expr. Purif.*, 2, 95-107 (1991).

*Primary Examiner* — Nancy T Vogel
*Assistant Examiner* — Catherine Hibbert
(74) *Attorney, Agent, or Firm* — Dorene M. Price

(57) ABSTRACT

Expression vectors for expression of a protein or polypeptide of interest as a fusion product composed of the protein or polypeptide of interest fused at one terminus to a solubility enhancing peptide extension are provided. Sequences encoding the peptide extensions are provided. The invention further comprises antibodies which bind specifically to one or more of the solubility enhancing peptide extensions.

4 Claims, 3 Drawing Sheets

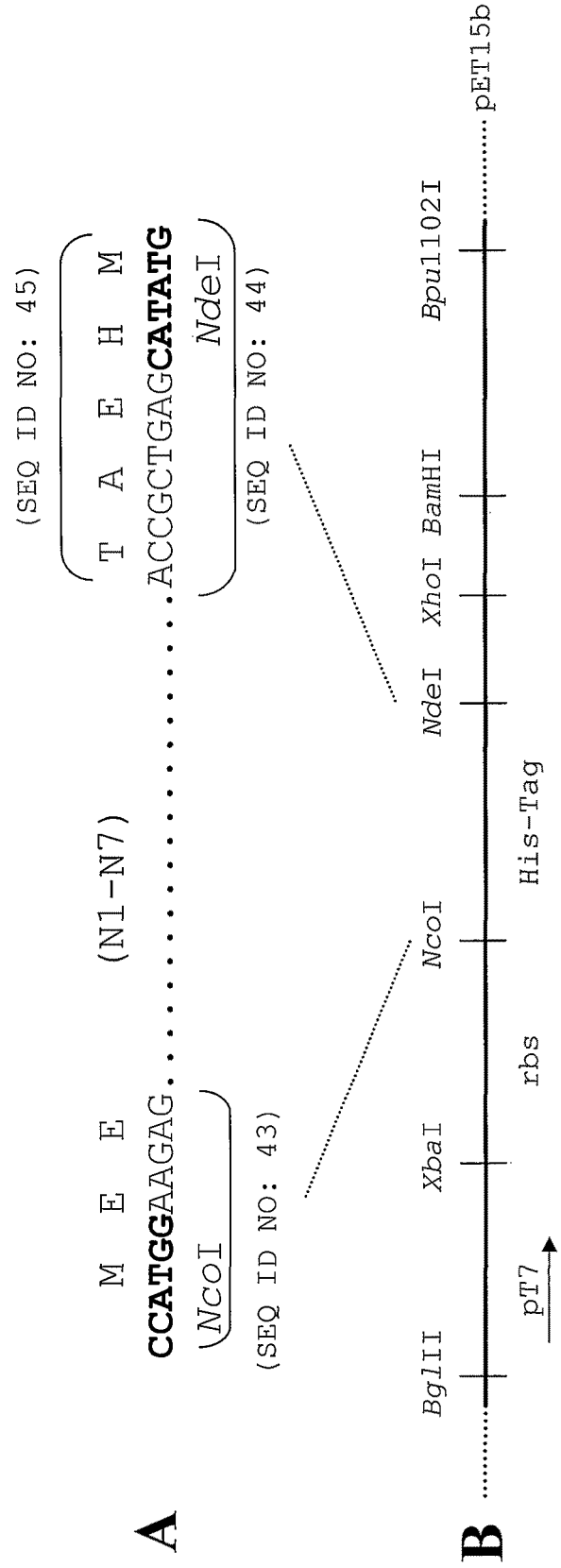

SEQUENCE LISTING

<160> NUMBER OF SEQ ID NOS: 50

<210> SEQ ID NO 1
<211> LENGTH: 57
<212> TYPE: PRT
<213> ORGANISM: Artificial Sequence
<220> FEATURE:
<223> OTHER INFORMATION: Description of Artificial Sequence: Synthetic
      bacteriophage T7 gene 10B protein

<400> SEQUENCE: 1

Phe Gln Ser Gly Val Met Leu Gly Val Ala Ser Thr Val Ala Ala Ser
1               5                   10                  15

Pro Glu Glu Ala Ser Val Thr Ser Thr Glu Glu Thr Leu Thr Pro Ala
            20                  25                  30

Gln Glu Ala Ala Arg Thr Arg Ala Ala Asn Lys Ala Arg Lys Glu Ala
        35                  40                  45

Glu Leu Ala Ala Ala Thr Ala Glu Gln
    50                  55

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 2

Ala Ala Asn Lys Ala Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      recognition motif

<400> SEQUENCE: 3

Ala Ala Asn Asp Glu Asn
1               5

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Leu Glu Asp Pro Ala Ala Asn Lys Ala Arg Lys Glu Ala Glu Leu
1               5                   10                  15

Ala Ala Ala Thr Ala Glu Gln
            20

<210> SEQ ID NO 5
<211> LENGTH: 61
<212> TYPE: PRT
<213> ORGANISM: Artificial Sequence
<220> FEATURE:
<223> OTHER INFORMATION: Description of Artificial Sequence: Synthetic
      T7C peptide

<400> SEQUENCE: 5

Leu Glu Asp Pro Phe Gln Ser Gly Val Met Leu Gly Val Ala Ser Thr
1               5                   10                  15

Val Ala Ala Ser Pro Glu Glu Ala Ser Val Thr Ser Thr Glu Glu Thr
            20                  25                  30

Leu Thr Pro Ala Gln Glu Ala Ala Arg Thr Arg Ala Ala Asn Lys Ala
        35                  40                  45

Arg Lys Glu Ala Glu Leu Ala Ala Ala Thr Ala Glu Gln
    50                  55                  60

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B peptide

<400> SEQUENCE: 6

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Arg
            20                  25                  30

Lys Glu Ala Glu Leu Ala Ala Ala Thr Ala Glu Gln
        35                  40

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      T7B1 peptide

<400> SEQUENCE: 7

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Arg
            20                  25                  30

Lys Glu Ala Glu Leu Thr Ala Glu Gln
        35                  40

<210> SEQ ID NO 8
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B2 peptide

<400> SEQUENCE: 8

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Pro Pro Asn Lys Ala Arg
            20                  25                  30

Lys Glu Ala Glu Leu Ala Ala Ala Thr Ala Glu Gln
        35                  40

<210> SEQ ID NO 9
<211> LENGTH: 44
<212> TYPE: PRT
<213> ORGANISM: Artificial Sequence

```
<220> FEATURE:
<223> OTHER INFORMATION: Description of Artificial Sequence: Synthetic
      T7B3 peptide

<400> SEQUENCE: 9

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Gly Gly Asn Lys Ala Arg
            20                  25                  30

Lys Glu Ala Glu Leu Ala Ala Ala Thr Ala Glu Gln
            35                  40

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      T7B4 peptide

<400> SEQUENCE: 10

Leu Glu Asp Pro Thr Pro Ala Gln Glu Ala Ala Arg Thr Arg Ala Ala
1               5                   10                  15

Asn Lys Ala Arg Lys Glu Ala Glu Leu Ala Ala Ala Thr Ala Glu Gln
            20                  25                  30

<210> SEQ ID NO 11
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B5 peptide

<400> SEQUENCE: 11

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Arg
            20                  25                  30

Lys Glu Ala Glu Leu Glu Ala Glu Thr Ala Glu Gln
            35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B6 peptide

<400> SEQUENCE: 12

Leu Glu Asp Pro Glu Glu Ala Ser Val Thr Ser Thr Glu Glu Thr Leu
1               5                   10                  15

Thr Pro Ala Gln Glu Ala Ala Glu Thr Glu Ala Ala Asn Lys Ala Arg
            20                  25                  30

Lys Glu Ala Glu Leu Glu Ala Glu Thr Ala Glu Gln
            35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B7 peptide
```

```
<400> SEQUENCE: 13

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Glu
            20                  25                  30

Glu Glu Ala Glu Leu Glu Ala Glu Thr Ala Glu Gln
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B8 peptide

<400> SEQUENCE: 14

Leu Glu Asp Pro Glu Glu Ala Ser Val Thr Ser Thr Glu Glu Thr Leu
1               5                   10                  15

Thr Pro Ala Gln Glu Ala Ala Glu Thr Glu Ala Ala Asn Lys Ala Glu
            20                  25                  30

Glu Glu Ala Glu Leu Glu Ala Glu Thr Ala Glu Gln
        35                  40

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      T7B9 peptide

<400> SEQUENCE: 15

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Arg
            20                  25                  30

Lys Glu Ala Glu Leu Ala Ala
        35

<210> SEQ ID NO 16
<211> LENGTH: 40
<212> TYPE: PRT
<213> ORGANISM: Artificial Sequence
<220> FEATURE:
<223> OTHER INFORMATION: Description of Artificial Sequence: Synthetic
      T7B10 peptide

<400> SEQUENCE: 16

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Ala Arg
            20                  25                  30

Lys Glu Ala Glu Leu Ala Ala Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      T7B11 peptide
```

-continued

```
<400> SEQUENCE: 17

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Ala Lys Ala Arg
            20                  25                  30

Lys Glu Ala Glu Leu Ala Ala Ala Thr Ala Glu Gln
        35                  40

<210> SEQ ID NO 18
<211> LENGTH: 41
<212> TYPE: PRT
<213> ORGANISM: Artificial Sequence
<220> FEATURE:
<223> OTHER INFORMATION: Description of Artificial Sequence: Synthetic
      T7B12 peptide

<400> SEQUENCE: 18

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Lys Ala Arg Lys Glu Ala
            20                  25                  30

Glu Leu Ala Ala Ala Thr Ala Glu Gln
        35                  40

<210> SEQ ID NO 19
<211> LENGTH: 41
<212> TYPE: PRT
<213> ORGANISM: Artificial Sequence
<220> FEATURE:
<223> OTHER INFORMATION: Description of Artificial Sequence: Synthetic
      T7B13 peptide

<400> SEQUENCE: 19

Leu Glu Asp Pro Glu Glu Ala Ser Val Thr Ser Thr Glu Glu Thr Leu
1               5                   10                  15

Thr Pro Ala Gln Glu Ala Ala Arg Thr Arg Ala Ala Asn Lys Glu Ala
            20                  25                  30

Glu Leu Ala Ala Ala Thr Ala Glu Gln
        35                  40

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A peptide

<400> SEQUENCE: 20

Leu Glu Asp Pro Ala Ala Asn Lys Ala Arg Lys Glu Ala Glu Leu Ala
1               5                   10                  15

Ala Ala Thr Ala Glu Gln
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A1 peptide

<400> SEQUENCE: 21
```

Leu Glu Asp Pro Glu Arg Asn Lys Glu Arg Lys Glu Ala Glu Leu Ala
1               5                   10                  15

Ala Ala Thr Ala Glu Gln
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A2 peptide

<400> SEQUENCE: 22

Leu Glu Asp Pro Glu Arg Asn Lys Glu Arg Lys Glu Ala Glu Leu Glu
1               5                   10                  15

Ala Ala Thr Ala Glu Gln
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A3 peptide

<400> SEQUENCE: 23

Leu Glu Asp Pro Glu Arg Asn Lys Glu Arg Lys Glu Ala Glu Leu Glu
1               5                   10                  15

Ala Glu Thr Ala Glu Gln
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A4 peptide

<400> SEQUENCE: 24

Leu Glu Asp Pro Ala Ala Asn Lys Ala Arg Lys Glu Ala Glu Leu Glu
1               5                   10                  15

Ala Ala Thr Ala Glu Gln
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      T7A5 peptide

<400> SEQUENCE: 25

Leu Glu Asp Pro Ala Ala Asn Lys Ala Arg Lys Glu Ala Glu Leu Glu
1               5                   10                  15

Ala Glu Thr Ala Glu Gln
            20

<210> SEQ ID NO 26
<211> LENGTH: 43
<212> TYPE: PRT
<213> ORGANISM: Artificial Sequence
<220> FEATURE:

```
<223> OTHER INFORMATION: Description of Artificial Sequence:  Synthetic
      T3 peptide

<400> SEQUENCE: 26

Leu Glu Asp Pro Ala Val Trp Glu Ala Gly Lys Val Val Ala Lys Gly
1               5                   10                  15

Val Gly Thr Ala Asp Ile Thr Ala Thr Thr Ser Asn Gly Leu Ile Ala
            20                  25                  30

Ser Cys Lys Val Ile Val Asn Ala Ala Thr Ser
        35                  40

<210> SEQ ID NO 27
<211> LENGTH: 41
<212> TYPE: PRT
<213> ORGANISM: Artificial Sequence
<220> FEATURE:
<223> OTHER INFORMATION: Description of Artificial Sequence:  Synthetic
      N1 peptide

<400> SEQUENCE: 27

Met Glu Glu Ala Ser Val Thr Ser Thr Glu Thr Leu Thr Pro Ala
1               5                   10                  15

Gln Glu Ala Ala Arg Thr Arg Ala Ala Asn Lys Ala Arg Lys Glu Ala
            20                  25                  30

Glu Leu Ala Ala Ala Thr Ala Glu His
        35                  40

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence:  Synthetic
      N2 peptide

<400> SEQUENCE: 28

Met Ala Glu Arg Ala Ser Val Thr Ser Thr Glu Glu Thr Leu Thr Pro
1               5                   10                  15

Ala Gln Glu Ala Ala Arg Thr Arg Ala Ala Asn Lys Ala Arg Lys Glu
            20                  25                  30

Ala Glu Leu Ala Ala Ala Thr Ala Glu His
        35                  40

<210> SEQ ID NO 29
<211> LENGTH: 42
<212> TYPE: PRT
<213> ORGANISM: Artificial Sequence
<220> FEATURE:
<223> OTHER INFORMATION: Description of Artificial Sequence:  Synthetic
      N3 peptide

<400> SEQUENCE: 29

Met Ala Glu Glu Ala Lys Val Thr Ser Thr Glu Glu Thr Leu Thr Pro
1               5                   10                  15

Ala Gln Glu Ala Ala Arg Thr Arg Ala Ala Asn Lys Ala Arg Lys Glu
            20                  25                  30

Ala Glu Leu Ala Ala Ala Thr Ala Glu His
        35                  40

<210> SEQ ID NO 30
<211> LENGTH: 42
<212> TYPE: PRT
<213> ORGANISM: Artificial Sequence
<220> FEATURE:
```

```
<223> OTHER INFORMATION: Description of Artificial Sequence:  Synthetic
      N4 peptide

<400> SEQUENCE: 30

Met Ala Glu Arg Ala Lys Arg Thr Ser Thr Glu Glu Thr Leu Thr Pro
1               5                   10                  15

Ala Gln Glu Ala Ala Arg Thr Arg Ala Ala Asn Lys Ala Arg Lys Glu
            20                  25                  30

Ala Glu Leu Ala Ala Ala Thr Ala Glu His
        35                  40

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence:  Synthetic
      N5 peptide

<400> SEQUENCE: 31

Met Glu Glu Ala Ser Val Thr Ser Thr Glu Thr Leu Thr Pro Ala
1               5                   10                  15

Gln Glu Ala Ala Arg Thr Arg Ala Ala Asn Lys Ala Arg Lys Glu Ala
            20                  25                  30

Glu Leu Glu Ala Glu Thr Ala Glu His
        35                  40

<210> SEQ ID NO 32
<211> LENGTH: 41
<212> TYPE: PRT
<213> ORGANISM: Artificial Sequence
<220> FEATURE:
<223> OTHER INFORMATION: Description of Artificial Sequence:  Synthetic
      N6 peptide

<400> SEQUENCE: 32

Met Glu Glu Ala Ser Val Thr Ser Thr Glu Thr Leu Thr Pro Ala
1               5                   10                  15

Gln Glu Ala Ala Glu Thr Glu Ala Ala Asn Lys Ala Arg Lys Glu Ala
            20                  25                  30

Glu Leu Glu Ala Glu Thr Ala Glu His
        35                  40

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence:  Synthetic
      N7 peptide

<400> SEQUENCE: 33

Met Glu Glu Ala Ser Val Thr Ser Thr Glu Thr Leu Thr Pro Ala
1               5                   10                  15

Gln Glu Ala Ala Arg Thr Arg Ala Ala Asn Lys Ala Glu Lys Glu Ala
            20                  25                  30

Glu Leu Glu Ala Glu Thr Ala Glu His
        35                  40

<210> SEQ ID NO 34
<211> LENGTH: 27
<212> TYPE: DNA
<213> ORGANISM: Artificial Sequence
<220> FEATURE:
```

```
<223> OTHER INFORMATION: Description of Artificial Sequence:
      Illustrative linker sequence

<400> SEQUENCE: 34
ccatgggtat cactactcct gaagaga                                              27

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:  Encoded
      amino acids

<400> SEQUENCE: 35

Met Gly Ile Thr Thr Pro Glu Glu
1               5

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:
      Illustrative linker sequence

<400> SEQUENCE: 36
taagccttca ggtgcgctcg ag                                                   22

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence:  Encoded
      amino acids

<400> SEQUENCE: 37

Lys Pro Ser Gly Ala Leu Glu
1               5

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence:
      Illustrative sequence

<400> SEQUENCE: 38
ctcgaggatc cg                                                              12

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Encoded
      amino acids

<400> SEQUENCE: 39

Leu Glu Asp Pro
1

<210> SEQ ID NO 40
<211> LENGTH: 12
<212> TYPE: DNA
<213> ORGANISM: Artificial Sequence
```

```
<220> FEATURE:
<223> OTHER INFORMATION: Description of Artificial Sequence:
      Illustrative sequence

<400> SEQUENCE: 40
gctgagcaat aa                                                            12

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence:  encoded
      amino acids

<400> SEQUENCE: 41

Ala Ala Asn Lys Ala Arg Lys Glu Ala Glu Leu Ala Ala Ala Thr
1               5                   10                  15

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Encoded
      amino acids

<400> SEQUENCE: 42

Leu Glu Asp Pro Ala Ala Asn Lys Ala Arg Lys Glu Ala Glu Leu Ala
1               5                   10                  15

Ala Ala Thr Ala Glu Gln
            20

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence:
      Illustrative coding sequence

<400> SEQUENCE: 43
ccatggaaga g                                                             11

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence:
      Illustrative coding sequence

<400> SEQUENCE: 44
accgctgagc atatg                                                         15

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Encoded
      amino acids

<400> SEQUENCE: 45

Thr Ala Glu His Met
1               5
```

```
<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Six His tag

<400> SEQUENCE: 46

His His His His His His
1               5

<210> SEQ ID NO 47
<211> LENGTH: 186
<212> TYPE: DNA
<213> ORGANISM: Artificial Sequence
<220> FEATURE:
<223> OTHER INFORMATION: Encodes peptide T7C

<400> SEQUENCE: 47
ctcgaggatc cgtttcaaag tggagtaatg ctggggtgg cctcaacggt cgctgctagt      60
cccgaagagg cgagtgttac ttcaacagaa gaaaccttaa cgccagcaca ggaggccgca    120
cgcacccgcg ctgctaacaa agcccgaaag gaagctgagt tggctgctgc caccgctgag    180
caataa                                                               186

<210> SEQ ID NO 48
<211> LENGTH: 69
<212> TYPE: DNA
<213> ORGANISM: Artificial Sequence
<220> FEATURE:
<223> OTHER INFORMATION: Encodes peptide T7A1

<400> SEQUENCE: 48
ctcgaggatc cggaacgcaa caaagagcga aggaagctg agttggctgc tgccaccgct      60
gagcaataa                                                             69

<210> SEQ ID NO 49
<211> LENGTH: 69
<212> TYPE: DNA
<213> ORGANISM: Artificial Sequence
<220> FEATURE:
<223> OTHER INFORMATION: Encodes peptide T7A2

<400> SEQUENCE: 49
ctcgaggatc cggaacgcaa caaagagcga aggaagctg agttggaggc tgccaccgct      60
gagcaataa                                                             69

<210> SEQ ID NO 50
<211> LENGTH: 69
<212> TYPE: DNA
<213> ORGANISM: Artificial Sequence
<220> FEATURE:
<223> OTHER INFORMATION: Encodes peptide T7A3

<400> SEQUENCE: 50
ctcgaggatc cggaacgcaa caaagagcga aggaagctg agttggaagc tgagaccgct      60
gagcaataa                                                             69
```

FACILITATING PROTEIN SOLUBILITY BY USE OF PEPTIDE EXTENSIONS

RELATED APPLICATIONS

The present application is a continuation in part of U.S. patent application Ser. No. 10/037,243 filed Jan. 4, 2002, the contents of which are incorporated herein by reference.

GOVERNMENT SUPPORT

This invention was made with Government support under contract number DE-AC02-98CH10886, awarded by the U.S. Department of Energy. The Government has certain rights in the invention.

FIELD OF THE INVENTION

The present invention relates to expression vectors for production of a protein or polypeptide of interest as a fusion product composed of the protein or polypeptide of interest fused at one terminus to a solubility enhancing peptide extension. In the expression vectors, novel peptide extensions are encoded in frame for fusion at the amino or carboxyl terminus of the protein or polypeptide of interest. Said novel peptides may also serve as affinity tags for purposes of isolation and purification of the expressed protein or polypeptide of interest. Thus, antibodies that specifically bind to the peptide extensions are also provided.

BACKGROUND OF THE INVENTION

Large quantities of biologically active proteins are required for studies of protein structure-function relationships and also for the development and use of proteins in medical or industrial applications. Recombinant DNA technology enables the expression of proteins to unusually high levels in various cell types. In bacterial recombinant protein expression systems, protein over-expression is typically accomplished by cloning a nucleic acid sequence (gene or cDNA) encoding the desired protein into a suitable plasmid expression vector to form an expression construct, transforming the bacterial cells with the expression construct and culturing the transformants under conditions suitable for expression of the cloned gene.

Expression vectors are very well known in the art. Typical bacterial expression vectors are designed to contain and encode regulatory sequences, e.g., promoters, ribosome binding sites, termination signals, and the like, which provide for vigorous transcription of the cloned DNA and translation of the corresponding mRNA into the desired protein. To facilitate cloning of nucleic acid sequences encoding the protein or polypeptide of interest, expression vectors further comprise a multiple cloning site (MCS), which typically is a sequence of several unique restriction endonuclease sites present only within the MCS and nowhere else in the vectors. In expression vectors the MCS is located downstream of RNA polymerase promoter sequences and is designed so that transcribed RNAs will contain the proper signals for ribosome binding such that translation of the RNA will initiate at the proper position. Expression vectors also generally include one or more selectable marker genes (e.g., antibiotic resistance factor), so that the cells which have been successfully transformed with the expression vector can be identified and separated from those cells which have not been transformed.

One of the most powerful bacterial expression systems, with respect to the amounts of the protein of interest that can be produced, is the T7 expression system (Moffatt, B. A. and Studier, F. W. J. Mol. Biol. 189:113-130 (1986)). In this system, a gene or cDNA sequence encoding the protein or polypeptide of interest is cloned into an MCS located downstream of the T7 RNA polymerase promoter in "T7 expression vectors", such as pET vectors (see Studier, et al., Met. Enzymology 185:60-89 (1990) and EMD Biosciences, Novagen; Stratagene; and Invitrogen product catalogs) and others, to form a recombinant T7 expression construct. Bacterial cells containing a gene for the T7 RNA polymerase (e.g., T7 expression system host strains such as BL21(DE3), EMD Biosciences, Novagen and others) are transformed with such recombinant T7 expression constructs. In the transformed cells, the T7 RNA polymerase specifically recognizes the T7 RNA polymerase promoter and rapidly generates extraordinarily large amounts of the corresponding mRNA transcript, leading to over-expression of the protein or polypeptide within the host cells. In this and similar bacterial expression systems, the desired protein or polypeptide may very quickly become the most predominant proteinaceous species in the host cell.

One of the most troublesome issues related to the expression of such large amounts of a recombinant protein is that many over-expressed proteins are unable to adopt a native, biologically-active conformation and thus become misfolded within the bacterial host cell. Generally misfolded proteins exhibit poor solubility and either accumulate in cells as insoluble aggregates (inclusion bodies) or are degraded by host cell proteases. By way of example of the generality of this problem, a recent simple search of the US patent database using Specification search terms "inclusion body" or "inclusion bodies" in combination with the terms "clone" and "expression" generated a list of 3,435 issued US patents. In most of these patents, recombinant proteins formed inclusion bodies during expression in various bacterial expression systems. The first patent in the hit list issued in February, 1987 and the most recent on the date the search was run, issued on Dec. 29, 2009. Thus, for over 22 years the failure of proteins to adopt native conformations during recombinant expression has been an issue for production of recombinant proteins. In other words, since the time recombinant protein expression became a more or less routinely practiced art, protein misfolding and lack of solubility has been problematic in generation of recombinant proteins.

Although most recombinant proteins that misfold are those that are non-native to the expression host cell, even native bacterial proteins can misfold and form insoluble aggregates during over-expression in bacterial recombinant protein expression systems.

The expression of the protein or polypeptide of interest as a fusion protein has been proposed as a method for averting protein misfolding and inclusion body formation (see Snavely, U.S. Pat. No. 6,077,689; Mascarenhas, et al. U.S. Pat. No. 5,563,046; Lima et al. U.S. Pat. No. 6,872,551; and Harrison, et al., U.S. Pat. Nos. 5,989,868 and 6,207,420). Considerable effort has also been devoted to the development of various fusion partners to either protect the protein or polypeptide of interest from degradation by host cell proteases or to provide a facile means of purification of the protein or polypeptide of interest (reviewed by Ford, et al., (1991) Prot. Exp. and Purif. 2:95-107). It has been suggested that such fusion elements may serve both functions: enhancement of the solubility and proper folding of the recombinant protein of interest and as a means for isolation and purification of the protein.

A significant drawback of such fusion systems for enhancing the solubility of recombinant proteins in the host cells is that none of the systems has demonstrated applicability to all or even a wide variety of proteins of interest. It is common that those skilled in the art will try several fusion partners for each target protein or polypeptide of interest to find one that produces the desired outcome. Another drawback to expression of a protein of interest as a fusion product includes the use of fusion partners that are large polypeptides, which results in decreased expression overall and an absolute and relative decrease in yield of the protein or polypeptide of interest. Yet another drawback is the need to engineer a specific cleavage site into the fusion protein so that the protein or polypeptide of interest can be separated from its fusion partner. The costs of the specific agent to effect that cleavage can be prohibitive.

Accordingly, there remains a need for the development of expression methodologies to ameliorate problems associated with poor solubility and misfolding during the over-expression of proteins in high yielding protein expression systems.

SUMMARY OF THE INVENTION

The present invention relates to expression vectors for production of proteins or polypeptides of interest (i.e., target proteins) as fusion products composed of the protein or polypeptide of interest fused at one terminus to a solubility enhancing peptide extension. Novel peptide extensions are encoded in frame for amino- or carboxyl-terminal fusion with the protein or polypeptide of interest.

In one embodiment the present invention relates to expression vectors comprising a nucleic acid sequence encoding a peptide extension of the type described herein, and a multiple cloning site (MCS) for inserting, in frame with the nucleic acid encoding the peptide extension, a nucleic acid sequence encoding a protein or polypeptide of interest (i.e., target protein).

In vectors encoding the peptide extensions for fusion at the amino terminus of the protein or polypeptide of interest, the sequences encoding the peptide extensions may located immediately upstream of the MCS or immediately upstream of the point of insertion of the sequence encoding the protein or polypeptide of interest. In vectors encoding the peptide extensions for fusion at the carboxyl terminus of the protein or polypeptide of interest, the sequences encoding the peptide extensions may be located immediately downstream of the MCS or immediately downstream of the point of insertion of the sequence encoding the protein or polypeptide of interest. In both instances, the vectors are designed so that the sequences encoding the peptide extensions are in frame with the sequences encoding the target protein that are inserted in the MCS.

An aspect of the invention includes isolated sequences encoding the peptide extensions. More particularly this aspect includes sequences encoding the peptide extensions prepared for easy insertion into various expression vectors.

Antibodies which specifically recognize and bind to the novel peptide extensions are also provided. Such antibodies may be useful in effecting rapid isolation of expression proteins or polypeptides of interest.

Panel A: Illustrates a schematic of the CAR structural organization.

Panel B: Illustrates the nucleic acid sequences of the forward PCR primer (SEQ ID NO: 34) and the complement of the reverse PCR primer (SEQ ID NO: 36) used to amplify CAR D1. Both primers were tailed with restriction sites (bold type) to facilitate cloning into the pET15b expression vector. The encoded amino acid residues (SEQ ID NOS: 35 and 37) are shown in single letter code.

Panel C: Illustrates the nucleotide sequences (SEQ ID NOS: 38 and 40) and amino acid sequences (SEQ ID NOS: 39 and 42) of the CAR D1-T7A fusion protein generated by insertion of the CAR D1 PCR product of panel B into the NcoI-XhoI-digested pET15b expression vector. The amino acid sequence of the resulting CAR D1-T7A fusion protein is shown in single letter code (SEQ ID NO: 41) on the top line (note that the central amino acid residues of CAR D1, from Ile 3 to Ala 125, are not shown, and are represented by . . . ). The translation termination signal (TAA) is indicated by an asterisk (*). Nucleotide sequences of restriction enzyme cleavage sites used to generate CAR D1 fusions with the peptide extensions are labeled and shown in bold type.

Figure 2:
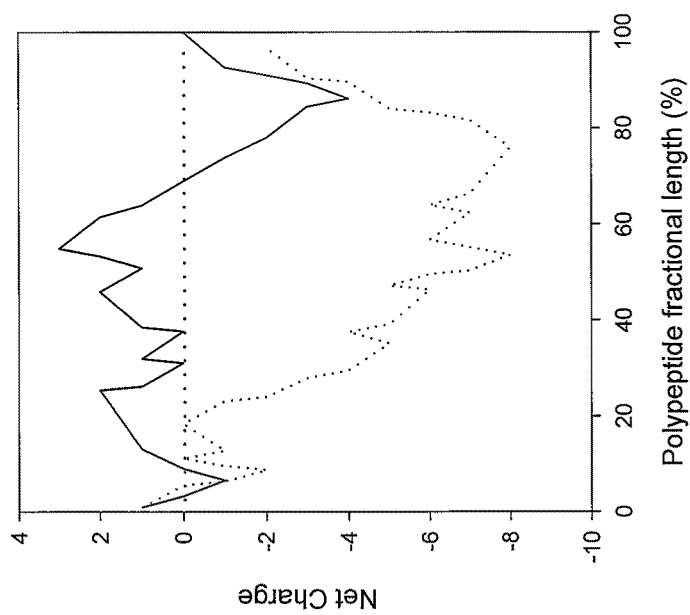

FIG. 2: Illustrates the integrated net charge of CAR D1 and A33 D1 polypeptides plotted against polypeptide fractional length. Running tally of polypeptide net charge (calculation based only upon D, E, R, and K residues) was plotted as a function of polypeptide fractional length (i.e., charged residue number/total length of polypeptide X 100). Solid line, A33 D1; Dotted line, CAR D1; Horizontal dotted line, position of uncharged species.

FIG. 3: Illustrates a schematic of the structure of vectors for fusion of a protein amino-terminus to peptide extensions. DNA fragments encoding the T7B peptide or various modified T7B peptides were amplified by PCR using primers that appended an upstream NcoI restriction site (SEQ ID NO: 43) and a downstream NdeI restriction site (SEQ ID NO: 44) and encoding the amino acid sequences as shown in A. The PCR products were then cloned between the NcoI and NdeI sites of pET15b as shown in B. In the final ligated products, the 6-His tag (SEQ ID NO: 46) (which is normally present in pET15b in the region between NcoI and NdeI sites) is replaced by the N-terminal peptides (SEQ ID NO: 45).

DETAILED DESCRIPTION OF THE INVENTION

The present invention relates to novel expression vectors for production of a protein or polypeptide of interest (target protein) as a fusion product composed of the protein or polypeptide of interest fused at one terminus to a solubility enhancing peptide extension. In the expression vectors, novel peptide extensions are encoded in frame for fusion at the amino or carboxyl terminus of the protein or polypeptide of interest, so as to enhance its solubility within a host cell (e.g., prokaryotic cells such as *Escherichia coli*, or eukaryotic host cells including yeast, insect and mammalian cells). The vectors may be used for expression of proteins or polypeptides which are readily soluble in the absence of having a fused peptide extension, and yet find particular application for expression of target proteins that are poorly soluble and/or are incapable of adopting a biologically active (i.e., native) conformation in the absence of fusion to a peptide extension of the present invention. The vectors may be used to express proteins or polypeptides of interest fused to the peptide extensions which then serve as affinity tags to facilitate rapid and efficient isolation and purification of the protein or polypeptide of interest. Antibodies that specifically bind to the peptide extensions are also provided. Another embodiment relates to methods and compositions which facilitate the in vitro refolding of denatured fusion proteins in cases where fusion of the protein carboxyl- or amino terminus to a peptide extension does not directly yield a soluble protein or polypeptide in vivo.

A primary objective of the present invention is to enhance the solubility and proper folding of recombinant proteins of interest expressed in host cells. Accordingly, this disclosure enables the production of biologically-active non-prokaryotic and prokaryotic proteins within host cells in quantities sufficient for biochemical and biophysical analyses, such as X-ray crystallography and for use in industrial and/or medical applications.

As demonstrated in the Exemplification section which follows, prokaryotic cells (e.g., *E. coli*), represent an important example of a host cell to which the invention applies. However, solubility problems and the formation of inclusion bodies are well-known in eukaryotic host cells as well. The fundamental principles embodied in the described vectors apply with equal force in a eukaryotic host cell background.

In general, the present invention relates to two types of fusions. In a first type, the peptide extension is attached at the carboxyl terminus of the protein or polypeptide of interest. In the second type, the peptide extension is attached at the amino terminus of the protein or polypeptide of interest.

In connection with the carboxyl terminal extension, the peptide extension carries a net negative charge which ranges from about −2 to about −20. The effect of the charged extension on the solubility or biological activity of the protein or polypeptide of interest can vary depending upon the magnitude of the net negative charge. Therefore, preferred ranges of from −2 to −4; from −5 to −9; from −10 to −14; and from −5 to −20 have been specifically described.

While not wishing to be bound by theory, it is thought that the strong repulsive force associated with the net negative charge of the peptide extension serves to segregate individual protein or polypeptide molecules following their release from the ribosome. This repulsion serves to provide enough time for the protein or polypeptide to assume their native conformation even at high protein concentration. In the absence of repulsive extension, the proteins tend to aggregate during the folding process forming insoluble inclusion bodies. See also, Zhang, et al. (2004) Prot. Exp. and Purif. 36:207-216.

Any of a number of peptide extensions disclosed herein may be encoded in the vectors described herein. Each of the peptide extensions represents a portion or a variant of the 57 residue carboxyl-terminal portion of the T7 10B protein (Condron, et al., J. Bacteriol. 173:6998-7003 (1991)). The present invention encompasses vectors encoding peptide extensions that include this 57 residue polypeptide, and portions and variants thereof, which retain the ability to enhance solubility of a protein or polypeptide of interest when expressed as a fusion product. Variants of the 57 residue polypeptide (or portions thereof) include polypeptides in which amino acid substitutions were made that varied the overall net negative charge of the peptide extension between −2 and −20.

Examples of specific peptide extensions include peptides T7C (SEQ ID NO: 5), T7B (SEQ ID NO: 6), T7B1 (SEQ ID NO: 7), T7B2 (SEQ ID NO: 8), T7B3 (SEQ ID NO: 9), T7B5 (SEQ ID NO: 11), T7B6 (SEQ ID NO: 12), T7B7 (SEQ ID NO: 13), T7B8 (SEQ ID NO: 14), T7B9 (SEQ ID NO: 15), T7B10 (SEQ ID NO: 16), T7B11 (SEQ ID NO: 17), T7B12 (SEQ ID NO: 18), T7B13 (SEQ ID NO: 19), T7A1 (SEQ ID NO: 21), T7A2 (SEQ ID NO: 22), T7A3 (SEQ ID NO: 23), T7A4 (SEQ ID NO: 24) and T7A5 (SEQ ID NO: 25), as shown in Table 1.

Sequences encoding the above peptide extensions are also provided as one embodiment of this invention. For facile insertion into various expression vectors the sequences include one or more PCR generated restriction endonuclease sites at the termini of the peptide extension sequences. For purposes of directional insertion, the one or more restriction sites at the 5' terminus differ from those at the 3' terminus.

The above relates primarily to expression vectors designed for fusion of the peptide extension is at the carboxyl terminus of the protein or polypeptide of interest. The present invention also provides expression vectors designed for fusion of the peptide extension at the amino terminus of the protein or polypeptide of interest. As demonstrated in the exemplification section which follows, the charge range identified to be useful in connection with this embodiment is from about +2 to about −20. As was discussed above, the degree of solubility enhancement varied depending upon the magnitude of the charge of the peptide extension. Preferred ranges of from −15 to −20; from −10 to −14; from −5 to −9; from −1 to −4; and from +2 to −1 are specified. Other than net charge, no critical structural features of the peptide extension have been observed.

The specific amino-terminal peptide extensions exemplified comprise solubility-promoting portions of the 57 residue carboxyl-terminal portion of the T7 gene 10B protein, or variants thereof designed for insertion in frame with a target sequence located downstream of the sequence encoded the amino-terminal peptide extension. Peptide extensions for fusion at the amino terminus of the protein or polypeptide of interest include the following peptides which appear in Table 1: peptides N1 (SEQ ID NO: 27), N2 (SEQ ID NO: 28), N3 (SEQ ID NO: 29), N4 (SEQ ID NO: 30), N5 (SEQ ID NO: 31), N6 (SEQ ID NO: 32) and N7 (SEQ ID NO: 33).

Sequences encoding the above peptide extensions are also provided as one embodiment of this invention. For facile insertion into various expression vectors the sequences include one or more PCR generated restriction endonuclease sites at the termini of the peptide extension sequences. For purposes of directional insertion, the one or more restriction sites at the 5' terminus differ from those at the 3' terminus.

In addition to the above, in cases in which the expressed fusion protein or polypeptide was not soluble in the host cell, the disclosed vectors for expression of proteins or polypeptides of interest as fusion products provide for enhanced in vitro renaturation of the fusion product. Following expression of the fusion protein in the host cell, inclusion bodies are isolated from lysates of the host cell. The isolated inclusion bodies are then contacted with a denaturing solution thereby denaturing the fusion protein. Solutions of urea or guanidine hydrochloride are examples of appropriate denaturing solutions. The fusion protein comprising the inclusion bodies is solubilized in a denatured form by the denaturing solution. The fusion protein is then suspended in a renaturation buffer (e.g., a buffered saline solution) by dilution or dialysis in order to allow the fusion protein to obtain its native conformation and solubility. Quantitative or improved recovery of soluble fusion product was observed compared to recovery of the unfused product.

When a large percentage of this completely soluble fraction is present in solution as aggregate material, heat denaturation treatment of this soluble aggregate material resulted in substantial disaggregation. This was observed even when working with extremely high concentrations of peptide extended protein (e.g., 1 mg/ml or higher).

The present invention relates to expression vectors which carry sequences encoding peptide extensions of the type described above. The expression vectors are specific for, or optimized for, use with prokaryotic cells. Features of such vectors which render them useful are well known to those skilled in the art. These features include, without limitation, multiple cloning sites (MCSs), transcription signals, translation signals, termination signals, and the like. The multiple cloning site facilitates the insertion of DNA encoding a protein or polypeptide of interest, in frame with the sequence encoding the peptide extension. The position of the multiple cloning site relative to the sequence encoding the peptide extension can be oriented such that the peptide extension is attached to the protein or polypeptide of interest at its amino terminus or at its carboxy terminus.

In another aspect, the present invention relates to antibodies (either monoclonal or polyclonal) which bind specifically to the peptide extensions. Such antibodies are useful, for example, in the isolation and purification of a fusion protein comprising such a peptide extension. Methods of making such antibodies are well known in the art. In preferred embodiments, the antibodies of the present invention are characterized by the ability to specifically bind one or more peptide extensions from the set described in Table 1.

EXEMPLIFICATIONS

In the following examples, the expression of the coxsackievirus adenovirus receptor (CAR) D1 domain was examined extensively in an effort to develop vectors encoding peptide extensions especially suited to enhancing solubility of the expressed fusion product. Methods for incorporation of the sequences encoding the various peptide extensions into the pET15b vector used herein are readily applicable to introduce the peptide extension sequences into any other expression vector.

Although the CAR protein was used to examine properties of suitable peptide extensions, their effect when fused to other proteins or polypeptides of interest is readily examined by insertion of sequences encoding such proteins into the MCS region of vectors encoding the peptide extensions, as was done in several examples set forth below.

The inability of the peptide extensions to result in complete solubility of all proteins or polypeptides of interest when over-expressed in *E. coli* is not surprising as such inability is common to all such "solubility enhancing" fusion partners. It is not unusual that several different peptide extensions or different fusion partners will need to be tested by the practitioner in order to discover a combination that provides for greatest solubility of the particular protein of interest. In addition to which peptide extension/fusion partner to use, fusion of any such extension or partner at the carboxy terminus is likely to provide a different result from fusion of that extension/partner at the amino terminus.

1. Generation of the pET15b-CAR D1 Construct

The cellular receptor for adenovirus type 2 (Ad2), and many other adenovirus serotypes, has been recently described. The receptor, encoded by a single gene on human chromosome 21, also serves as the cellular receptor for group B coxsackieviruses (CBV; Tomko, et al., Proc. Natl. Acad. Sci. U.S.A. 94: 3352-3356 (1997)). Accordingly, this receptor was designated the coxsackievirus and adenovirus receptor (CAR). CAR is a 46 kiloDalton (kDa) member of the immunoglobulin-superfamily (IgSF) that possesses an extracellular aspect comprising of an amino-terminal domain (D1) which has a protein fold related to that of immunoglobulin (Ig) variable domains, and an adjacent domain (D2) whose fold is related to that of Ig constant region domains. CAR has a single, hydrophobic, membrane-spanning region and a ~100 residue cytoplasmic domain. (Bergelson, et al, Science 275: 1320-1323 (1997); Tomko, et al., (1997)). The structural organization of the CAR domains is illustrated schematically in FIG. 1, Panel A.

The pET15b vector (EMD Biosciences, Novagen) was derived, in part, from the bacteriophage T7 gene 10 transcription unit and includes a DNA sequence which contains both the transcription terminator and the last 18 codons (codons 381-398) of the T7 gene 10B protein (Studier, et al. (1990)).

A complementary DNA (cDNA) fragment encoding the CAR D1 domain was amplified by polymerase chain reaction (PCR) and cloned into the NcoI and XhoI sites of expression vector pET15b (Freimuth, et al., J. Virol. 73: 1392-1398 (1999)). The resulting construct was designated pET15b-CAR D1.

Figure 1:
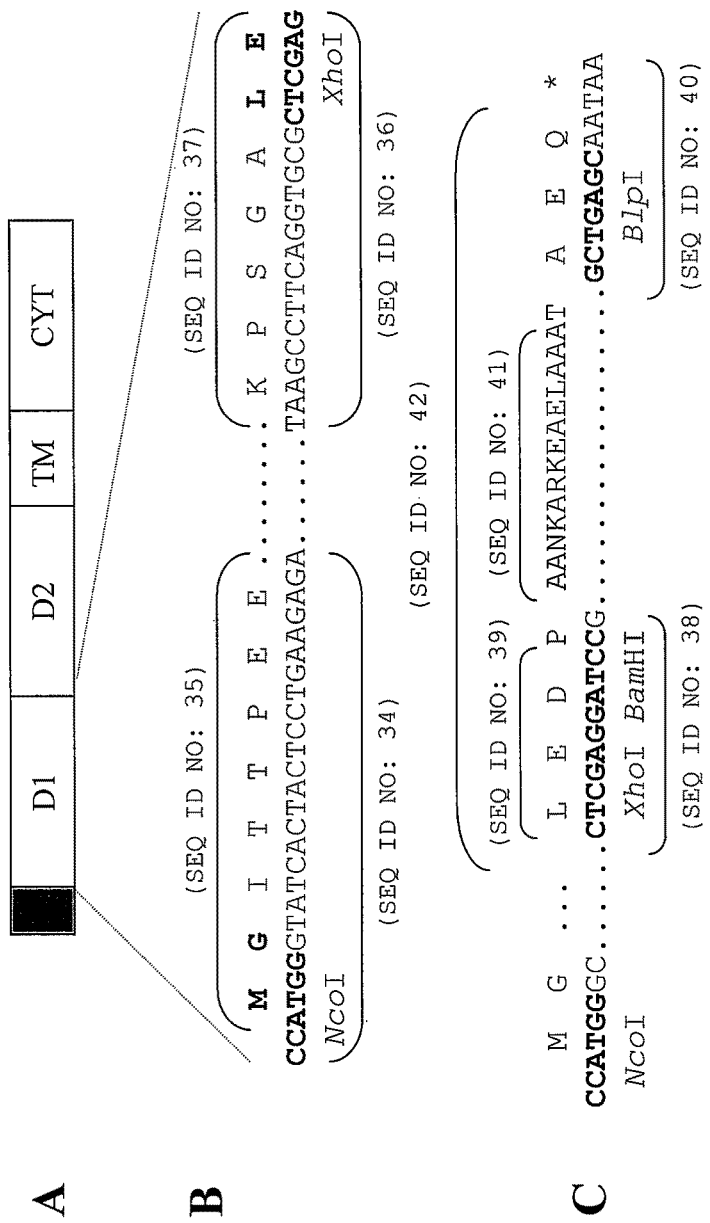
FIG. 1: Illustrates the schematic organization of the coxsackievirus and adenovirus receptor (CAR) and expression constructs used for expression of the D1 and D1/D2 domains.

More specifically, a cDNA fragment encoding the human CAR D1 domain was obtained by reverse-transcription PCR (RT-PCR) amplification of total RNA from murine A9 cells that were transfected with the cloned human CAR gene. The nucleotide sequence of the CAR D1-encoding cDNA fragment corresponded exactly to the CAR cDNA sequence reported in GenBank file Y07593. First-strand cDNA synthesis was primed with oligo(dT). Forward and reverse PCR primers were then used to amplify the cDNA fragment encoding CAR D1. Sequences of the PCR primers used are shown in FIG. 1, Panel B. Restriction sites for NcoI and XhoI (shown in bold type) were incorporated into the forward and reverse PCR primers to facilitate cloning into the pET15b expression vector. Following digestion with the restriction endonucleases NcoI and XhoI, the cDNA fragment encoding CAR D1 was cloned into the NcoI and XhoI sites of expression vector pET15b. The resulting construct was designated pET15b-CAR D1.

In the pET15b-CAR D1 expression vector construct (FIG. 1, panel C), fortuitously, the 3'-terminus of the CAR D1 cDNA fragment and the last 18 codons of T7 gene 10B were joined in frame to create a fusion protein in which the carboxyl terminus of CAR D1 was fused to the 22 amino acid T7 A peptide (SEQ ID NO: 20) shown in Table 1.

2. Expression of the CAR D1-T7A Fusion Protein

Expression of the CAR D1-T7A fusion protein from the pET15b-CAR D1 construct was performed as follows. The pET15b-CAR D1 construct was transformed into *Escherichia coli* strain BL21 (DE3) (EMD Biosciences, Novagen). Freshly transformed colonies were used to inoculate Luria-Bertani (LB) broth containing 150 mg/L penicillin G (Sigma), and the culture was grown at 37° C. until mid-log phase (optical density approximately 0.8 at 600 nm). The culture was then chilled to 18° C. and adjusted to 50 μM isopropyl D-thiogalactopyranoside (IPTG; Sigma) to induce protein expression. After incubation for an additional 5-20 hr at 18-20° C., the cells were harvested and analyzed for expression of CAR D1. Cells were lysed by several cycles of rapid freezing and thawing in the presence of lysozyme, followed by sonic disruption with a probe tip sonicator (Heat Systems, Inc.). Lysates were then centrifuged, and the supernatant fraction was transferred to a fresh tube. Protein content in both the soluble (supernatant) and insoluble (pellet) fractions was examined by SDS-PAGE (electrophoresis in polyacrylamide gels in the presence of sodium dodecylsulfate).

As cloned, the CAR D1 was fused to the 22 residue T7A peptide extension (SEQ ID No: 20), and approximately 50% of the fusion CAR D1 product was present in the soluble fraction of cell lysates, whereas the remainder of the CAR D1 fusion product was present in the insoluble pellet fraction (which contained macroscopic inclusion bodies). In contrast, when the 22 residue peptide extension was eliminated by insertion of a stop codon upstream of the XhoI cloning site, the CAR D1 fusion protein was completely aggregated in insoluble inclusion bodies (Freimuth, et al. (1999)).

The CAR D1-T7A fusion protein was purified from the soluble fraction of induced cell lysates by precipitation with ammonium sulfate (35 to 60% cut at 25° C.) followed by anion-exchange chromatography (on DE52, Whatman) in 10 mM Tris-HCl buffer (pH 7.5). Approximately 5 mg of partially-purified CAR D1-T7A fusion protein was recovered from 1 liter of culture.

The peptide extension could be removed from the soluble, purified CAR D1-T7A fusion protein by limited proteolytic-digestion with trypsin, and the resultant trypsin-stable CAR D1 fragment remained in solution and was biologically-active (Bewley, et al., Science 286: 1579-1583 (1999)). Thus, these initial studies demonstrated that the T7A peptide extension (SEQ ID NO: 20) mediated the partial solubilization and folding of CAR D1 into its biologically active conformation in E. coli.

3. Specificity of the Peptide-Mediated Solubility of CAR D1

Additional experiments were performed in order to establish whether the CAR D1 solubility enhancement was specific for bacteriophage T7 gene 10B-derived peptides such as the T7A peptide (SEQ ID NO: 20).

The bacteriophage T7 gene 10 encodes two proteins, 10A and 10B, which are identical in amino acid sequence for the first 342 amino acid residues. When translation terminates at the 345$^{th}$ (termination) codon the 10A protein is produced. When a reading frame shift occurs at codon 343 the 10B form of the gene 10 protein is produced. The frame shift occurs during translation at a rate of approximately 10%. When the frame shift occurs, translation continues for a total of 56 additional codons before terminating after codon 398 (Condron, et al., J. Bacteriol. 173: 6998-7003 (1991)). The sequence of the carboxyl-terminal 57 amino acid residues of the bacteriophage T7 gene 10B protein (amino acid residues 343-398) is (SEQ ID NO: 1)
FQSGVMLGVASTVAASPEEASVTSTEETLTPAQEAARTRAANKARKEAEL

AAATAEQ.

The bacteriophage T7 gene 10A and 10B proteins are structural proteins that form the icosahedral phage head. The unique 57 residue carboxyl-terminus of the 10B protein is exposed on the surface of phage heads, but this peptide is not essential for propagation of bacteriophage T7 under laboratory conditions. Indeed, in the bacteriophage T7-based phage display system (see EMD Biosciences, Novagen catalog and Studier, et al. U.S. Pat. No. 5,766,905), foreign peptides are substituted for the non-essential 10B C-terminal 57 residue peptide, and thus become displayed on the phage head.

Bacteriophage T3 (a close relative of T7) also has two forms of its major capsid protein (these bacteriophage T3 proteins are also named the gene 10A and 10B proteins) that are generated by a similar frame shift event (Condreay, et al., J. Mol. Biol. 207: 555-561 (1989)). However, the carboxyl-terminal peptides of the T3 and T7 gene 10B proteins are conserved neither in amino acid sequence (see Table 1) nor in length (89 residues in T3 vs 57 residues in T7).

To investigate the specificity of the T7A peptide-mediated folding of CAR D1, the effects of bacteriophage T7 and T3 gene 10B-derived, carboxyl-terminal peptide extensions on the folding of CAR D1 were compared. The DNA fragment encoding 18 amino acid residues of the T7A peptide (SEQ ID NO: 20) was excised from the pET15b-CAR D1 construct by digestion with restriction endonucleases BamHI and B/pI (see, FIG. 1, Panel C) and replaced with PCR products encoding either: (i) the complete 57 amino acid residue T7 gene 10B terminal peptide (T7C) (SEQ ID NO: 5); (ii) a shorter fragment encoding the last 40 amino acid residues of the T7 gene 10B terminal peptide (T7B) (SEQ ID NO: 6); or (iii) a fragment encoding the last 39 amino acid residues of the bacteriophage T3 gene 10B terminal peptide (T3) (SEQ ID NO: 26). These peptide extensions were designated peptide T7C (SEQ ID NO: 5), peptide T7B (SEQ ID NO: 6), and peptide T3 (SEQ ID NO: 26), respectively. The amino acid sequences of these peptide extensions are shown in Table 1.

Fusion of CAR D1 to either of the longer T7-derived peptide extensions (i.e., T7B and T7C) rendered the CAR D1 fusion product completely soluble, even when protein expression was induced at 37° C. In contrast, CAR D1 remained completely insoluble when fused to the T3-derived peptide extension. As shown in previous experiments, CAR D1 devoid of any carboxyl-terminal peptide extension was completely insoluble, whereas the CAR D1 protein was only partially soluble when fused to the initial 22 residue T7A peptide extension.

As for peptide T7A, peptide T7B could be cleaved from the soluble CAR D1 fusion product by limited proteolysis with trypsin. Furthermore, the resultant trypsin-stable CAR D1 protein was capable of binding specifically to the adenovirus fiber knob domain and was also recognized by antibodies prepared against CAR D1. In contrast, the CAR D1-T3 fusion protein isolated from inclusion bodies was completely hydrolyzed by low concentrations of trypsin, indicating that the CAR D1 component of this fusion protein was misfolded. Accordingly, the two longer T7-derived peptides, but not the T3-derived peptide, are able to mediate quantitative solubility and proper folding of CAR D1 into its biologically-active conformation in E. coli.

The failure of the T3-derived peptide to mediate CAR D1 folding suggested that the folding of CAR D1 results from some characteristic(s) of the T7 peptides that is not shared by the T3 peptide extension. In support of this view, the T3 and T7 terminal peptides share no obvious sequence homology (Table 1). Because fusion of CAR D1 to the two longer T7-derived peptides (T7B and T7C) resulted in 100% solubilization and folding, this analysis also suggests that Peptides T7B and T7C contain a feature(s) or characteristic(s) that is (are) not present or only partially present in the shorter 22 amino acid T7A peptide. Experiments were performed to examine the basis for the complete CAR D1 folding activity of the two longer peptides, as described herein below.

4. Mechanism of Protein Folding by T7-Derived Peptide Extensions

A. Role of Predicted Amphipathic α-Helices.

Both the T7B and T7C peptides were predicted by sequence analysis algorithms (e.g., Chou/Fasman) to contain two long α-helices, both of which have weak amphiphilic character as revealed by helical wheel projections. It is conceivable that peptide extensions with weak amphiphilic character could function as cis-acting chaperones by interacting transiently with hydrophobic regions of the newly translated polypeptide to prevent aggregation. Accordingly, peptide extension variants were constructed by PCR-mediated mutagenesis to determine if amphiphilic α-helical character is necessary for the protein folding activity of these peptides. Peptides T7B2 (SEQ ID NO: 8) and T7B3 (SEQ ID NO: 9) incorporate helix-disrupting proline or glycine residues at the start of the predicted carboxyl-terminal helix, whereas Peptide T7B1 (SEQ ID NO: 7) has a deletion that would disrupt the amphiphilic character of the predicted helix. When CAR D1 was expressed as a fusion product with each of these peptide variants, the yield of soluble CAR D1 fusion product was the same as for fusion to T7B or T7C, demonstrating that the solubilizing activity of the T7B and T7C peptide extensions does not depend on the ability of these peptides to form amphiphilic α-helices.

B. Recruitment of Trans-Acting Chaperones.

Experiments were performed to test whether the T7B peptide functions by recruiting chaperones to the nascent fusion protein, thus enhancing its folding. Neither the ClpB chaperone, which has been shown to mediate reversal of heat shock-induced protein aggregation in both yeast and bacterial cells (Glover and Lindquist, Cell 94: 73-82 (1998); Parsell, et al., Nature 372: 475-478 (1994)) nor the ssrA/SspB/ClpX system (Keiler, et al., Science 271: 990-993 (1996); Tu, et al., J. Biol. Chem. 270: 9322-9326 (1995); Levchenko, et al., Science 289: 2354-2356 (2000); Williams, et al., Mol. Microbiol. 11: 1029-1043 (1994)) appear to be involved in mediation of solubility of the T7B fusion product of CAR D1.

To examine whether the T7B peptide acts through a mechanism that is dependent upon binding by SspB and/or ClpX, additional variants of the T7B peptide were constructed in which critical residues of the putative recognition sites for either SspB (i.e., Peptide T7B11 (SEQ ID NO: 17) and Peptide T7B12 (SEQ ID NO: 18)) or ClpX (i.e., Peptide T7B9 (SEQ ID NO: 15) and Peptide T7B10 (SEQ ID NO: 16)) were altered or deleted. The yield of soluble CAR D1 fusion product was not reduced by any of these changes, indicating that these trans-acting factors do not contribute to the mechanism of T7B-mediated folding of CAR D1.

C. Role of Peptide Net Charge.

During analysis of T7 peptide variants generated for the studies described above, it was observed that the partial solubilizing activity of peptide T7A (SEQ ID NO: 20) was increased by substitutions to form peptide T7A1 (SEQ ID NO: 21), and, conversely, that the full solubilizing activity of peptide T7B (SEQ ID NO: 6) was reduced by shortening the sequence to form peptide T7B4 (SEQ ID NO: 10). The T7A1 (SEQ ID NO: 21) variant was constructed to disrupt the weak amphiphilic character of the peptide, whereas a T7B4 (SEQ ID NO: 10) variant was constructed to probe the length-dependence of the solubilizing activity. However, as shown in Table 1, the change to form Peptide T7A1 (SEQ ID NO: 21) increased the peptide net charge from −3 to −4, whereas the deletion to form Peptide T7B4 (SEQ ID NO: 10) decreased the peptide net charge from −6 to −2. Based on these results, additional variants were constructed in order to systematically examine whether there was a correlation between peptide net charge and ability to mediate solubilization of CAR D1. The relative proportion of soluble CAR D1 fusion product produced in E. coli increased as the net negative charge on peptide T7A (SEQ ID NO: 20) was increased from −3 to −6 (peptides T7A1 (SEQ ID NO: 21), T7A2 (SEQ ID NO: 22), and T7A3 (SEQ ID NO: 23)). Both peptides T7A3 (SEQ ID NO: 23) and T7B (SEQ ID NO: 6) were found to produce almost a 100% yield of soluble CAR D1 fusion product, and both species had a net negative charge of −6. Therefore, the characteristic of the carboxyl terminal peptide extensions that appears critical for their ability to mediate solubilizing of CAR D1 appears to be the net negative charge carried by the peptide extension. Consistent with this conclusion, the T3 peptide (SEQ ID NO: 26) extension, which is unable to fold CAR D1, has a net charge of −2.

5. Applicability of Carboxyl-Terminal Extensions to Other Test Proteins.

Peptide extensions that carry a large net negative charge will significantly alter the associated protein's isoelectric point (pI). In cases where isolated domains of multidomain proteins are being expressed (as is case for the present example of CAR D1), if the isoelectric point of the isolated domain is close to neutral, then the domain may have limited solubility in neutral pH solvents, such as the bacterial cytoplasm. Decreasing the pI of such proteins or protein fragments by attaching a peptide extension with a large net negative charge may increase the solubility of these proteins or protein fragments. According to this suggested model, since pI is an intrinsic property that varies from protein to protein, the solubilizing activity of a particular charged peptide extension (e.g., Peptide T7B) would be expected to vary depending upon the pI of the fused protein of interest. Alternatively, if the clustered negative charges in the peptide extension are recognized by trans-acting factors (i.e., other than ClpB, SspB, or ClpX) that promote protein folding, then a particular peptide may exhibit universal folding-activity when fused to many different proteins that normally are insoluble when over-expressed in E. coli.

In order to distinguish between these two possible mechanisms, the effect of peptide extensions on the folding of other test proteins was examined. In one experiment, the distal domain of the human A33 protein (Heath, et al., Proc. Natl. Acad. Sci. U.S.A. 94: 469-474 (1997)), the protein that is most similar to CAR D1 as revealed by homology searching using the BLAST-P program (32% identical), was examined. A33 and CAR are both members of the immunoglobulin superfamily and have similar protein and gene organization. See, Chretien, et al., Eur. J. Immunol. 28: 4094-4104 (1998). A cDNA fragment encoding the A33 distal domain (D1) was amplified by PCR and cloned into the pET15b-T7A construct in the same manner as schematically illustrated in FIG. 1 for CAR D1. When a stop codon was included to prevent fusion to the T7 peptide, the expressed A33-D1 protein was found to be insoluble, as had been the case for CAR D1. However, unlike the results obtained with CAR D1, extending the carboxyl terminus of A33 D1 with the T7B peptide (SEQ ID NO: 6) did not increase A33 D1 solubility. Therefore, the T7B peptide (SEQ ID NO: 6) does not appear to universally promote protein solubilization in vivo, supporting the conclusion that these peptides do not function by recruiting chaperones to the misfolded protein.

To determine if further increasing the peptide extension net negative charge would enhance folding of A33-D1, the A33-D1 domain was fused to peptide T7B7 (SEQ ID NO: 13), which has a net charge of −12. The A33-D1-T7B7 fusion product was distributed approximately equally between the soluble and insoluble fractions of cell lysates. Only a slight further increase in fusion protein solubility resulted when A33-D1 was fused to Peptide T7B8 (SEQ ID NO: 14) which has a net charge of −16. Because the function of A33 is unknown and consequently there is no assay for its biological activity, the A33-D1-T7B7 conformation was characterized by limited proteolysis. Staphylococcal V8 protease digested the T7B7 (SEQ ID NO: 13) peptide extension more readily than it digested the A33-D1 domain, as was observed for CAR D1 fusion proteins, generating digestion products which migrated with slightly faster mobility than the intact protein in SDS-PAGE. However, unlike CAR D1, the A33-D1 domain and the T7B7 (SEQ ID NO: 13) peptide extension were equally sensitive to digestion with trypsin. Thus, although the A33-D1-T7B7 fusion protein is soluble, it may have a non-native conformation. This was further supported by the observation that the A33-D1-T7B7 fusion protein resolves into several species with distinct mobilities when electrophoresed under non-denaturing conditions. Together these results suggested that although the carboxyl-terminal peptide extension was able to partially solubilize A33-D1, it may not be able to mediate proper folding of the domain. Concomitant control experiments showed that both peptides T7B7 (SEQ ID NO: 13) and T7B8 (SEQ ID NO: 14) promote solubilization and folding of CAR D1 into its biologically active conformation, indicating that these peptides are compatible with in vivo folding of some proteins.

The analysis was extended to determine if the solubilization of other proteins could be enhanced in vivo by fusing the proteins at their carboxyl termini with the T7B peptide (SEQ ID NO: 6) and more highly charged derivatives (T7B5-T7B8) (SEQ ID NOS: 11, 12, 13, 14, respectively).

The $E.\ coli$ ClpX protein, a ~50 kD chaperone, aggregates into inclusion bodies when over-expressed in $E.\ coli$ using pET expression vectors. ClpX represents an example of how the conditions of protein over-expression can render $E.\ coli$ unable to properly fold even its own endogenous proteins when they are over-expressed.

Fusion of the ClpX at the carboxyl terminus to T7B (SEQ ID NO: 6) or to any of T7B5 through T7B8 (SEQ ID NOS: 11-14, respectively) peptides increased the fraction of the protein that was recovered in the soluble fraction of cell lysates. In contrast to the results obtained with A33, the carboxyl-terminal peptide extensions could be readily cleaved from the ClpX protein by limited proteolysis with both trypsin and V8 protease. Furthermore, after proteolytic removal of the T7B (SEQ ID NO: 6) carboxyl-terminal extension, the resulting processed ClpX protein had full biological activity both in terms of ATPase activity and ability to cooperate with the ClpP proteasome in degrading model protein substrates.

A group of thirteen yeast proteins which were known to form inclusion bodies when over-expressed in $E.\ coli$ using pET expression vectors were separately fused at their carboxyl termini to the T7B (SEQ ID NO: 6) peptide extension. Solubility of six of these proteins was rescued to greater than 50%, while another two were rescued to a lesser extent. Solubility of the remaining five proteins was not measurably affected by either the T7B peptide (SEQ ID NO: 6) or the T7B7 peptide (SEQ ID No: 13) (Table 2).

Thus, similar to other fusion partners known in the art, these peptide extensions were variously useful in promoting solubility and proper folding in vivo at a success rate of approximately 50%, half of the protein fusion products becoming soluble and the other half being unaffected by fusion at the carboxyl terminus with the peptide extensions.

6. Effect of N-Terminal Extensions on Protein Folding In Vivo.

By way of example and not of limitation, one possible mechanism for the carboxyl-terminal peptide extension-mediated folding of the over-expressed proteins of the present invention is that the strong repulsive force between highly-charged peptide extensions blocks aggregation of nascent proteins. The tendency for nascent polypeptide chains to aggregate during protein over-expression could result from a deficit of chaperones, as already discussed above. If a chaperone deficit does exist during protein over-expression, then it logically follows that nascent polypeptide chains synthesized under these conditions may be more exposed to solvent than they are under normal conditions when sufficient chaperones are available to shield nascent polypeptides from solvent (cytoplasm). Just as the solubility of native proteins varies with pH of the solvent (e.g. protein solubility approaches a minimum as the pH of the solvent approaches the protein isoelectric point), the solubility of nascent polypeptide chains that are partially or completely exposed to solvent during over-expression also may vary depending on the effective net charge of the protein species. If nascent polypeptides are exposed to solvent during their synthesis on ribosomes under conditions of over-expression, then the amount of exposed net charge also may vary as the nascent polypeptide emerges vectorially from the ribosome. According to this model, it is conceivable that unshielded nascent polypeptides may begin to precipitate co-translationally at times when the growing polypeptide chain carries little or no net charge, and that these minimally soluble species might aggregate upon release from ribosomes to form inclusion bodies. Blocking or inhibiting aggregate formation by carboxyl-terminal charged peptide extensions may provide time for the solvent-exposed, nascent polypeptide to proceed along the folding pathway and ultimately adopt the native state.

According to this model, it is reasonable to expect that the solubility of nascent polypeptides also could be altered by amino-terminal peptide extensions, and that this might be an alternative approach to avoiding protein aggregation in vivo. For example, if the integrated net charge of CAR D1 is plotted versus amino acid residue number (FIG. 2), one finds that the nascent polypeptide would exist as an uncharged species after synthesis of the protein was approximately 20% complete, i.e. at this point the number of positively charged and negatively charged amino acids in the growing nascent chain would be equal. If the nascent CAR D1 polypeptide is completely exposed to solvent at this point, then its solubility would be at or close to a minimum value. It is conceivable that the nascent CAR D1 polypeptide might begin to precipitate or even form small intermolecular aggregates on polyribosomes at this stage, and that these forms might be the precursors to the inclusion bodies that eventually form. However, the point at which the nascent CAR D1 polypeptide becomes an uncharged species could be altered or avoided entirely by fusion of the CAR D1 N-terminus to peptides that carry an appropriate net charge, thus avoiding co-translational precipitation of CAR D1 and the formation of inclusion bodies.

This model was tested by fusing the CAR D1 amino terminus to amino-terminal peptide extensions, according to the method outlined in FIG. 3. Consistent with the model, CAR D1 was least soluble when fused to the amino-terminal peptide extensions N2 and N3 (which have neutral or +1 net charges, respectively). By contrast, CAR D1 was mostly soluble when fused to the amino-terminal peptides N1 (SEQ ID NO: 27) and N4 (SEQ ID NO: 30), which have net charges of −2 and +2, respectively.

Results of fusion with other proteins were not completely consistent with this model, however. For example, the solubility of the 50 kD ClpX protein was significantly increased by fusion to the N-terminal peptide extension N2. Because the N2 peptide (SEQ ID NO: 28) has no net charge, it seems unlikely that this peptide could rescue of the folding of ClpX by a mechanism dependent on peptide net charge. Rather, in this case the N-terminal peptide extension may alter the initial folding pathway of the nascent polypeptide, fortuitously avoiding the formation of folding intermediates that may precipitate or be minimally soluble under conditions of chaperone deficit. Alternatively, the amino-terminal peptides may recruit chaperones to the nascent polypeptide chain.

7. Effects of Peptide Extensions on In Vitro Renaturation

During in vitro refolding of aggregated proteins, precipitation and aggregation of the protein upon removal of the denaturing agent is a common side reaction. Since carboxyl-terminal peptide extensions which carry a large net negative charge inhibit protein aggregation in vivo, possibly by electrostatic charge repulsion between nascent polypeptide chains, experiments were performed to investigate whether such peptide extensions could inhibit protein re-aggregation following protein refolding reactions in vitro. To test this hypothesis, the A33-D1 protein fragment was produced in 2 different forms, with or without a T7B6 peptide (SEQ ID NO:

12) carboxyl-terminal extension. Both forms of the A33-D1 protein were produced with an amino-terminal 6-histidine tag. When protein expression was induced at 37° C., both A33-D1 and A33-D1-T7B6 proteins accumulated in inclusion bodies (note that A33-D1-T7B6 is only partially soluble when induction is carried out at temperatures below 25° C.).

Inclusion bodies of A33-D1 and A33-D1-T7B6 were isolated, separately, from cell lysates by differential centrifugation, and dissolved in 8M guanidine hydrochloride (GuHCl). The solubilized proteins were then diluted with 10 volumes of renaturation buffer (10 mM Tris, 1 mM DTT, pH 8), incubated for approximately 2 hours at 4° C. to permit protein renaturation, and then dialyzed against renaturation buffer to remove the residual GuHCl denaturant. A large precipitate formed immediately upon dilution of the solubilized A33-D1 inclusion body into renaturation buffer, whereas the solubilized A33-D1-T7B6 fusion protein remained quantitatively in solution after dilution into renaturation buffer (the concentration of both proteins were approximately identical during, the refolding reaction). After dialysis, the preparations were centrifuged to pellet the insoluble material, and the protein content of the supernatant and pellet fractions were examined by denaturing (sodium dodecyl sulfate, SDS) polyacrylamide gel electrophoresis (PAGE).

Approximately 50% of the non-peptide-extended A33-D1 protein re-precipitated during the refolding process, whereas the peptide T7B6-extended protein was quantitatively recovered in soluble form. Analysis of the soluble products of the refolding reactions by electrophoresis under non-denaturing conditions showed that a small percentage of the refolded A33-D1-T7B6 migrated at a position similar to that of CAR D1, while the majority failed to migrate into the gel probably due to formation of small protein aggregates. By contrast, the refolded-A33 D1 protein without the T7B6 extension appeared to migrate entirely as aggregated species.

When the soluble A33-D1-T7B6 material was further analyzed by size exclusion chromatography, it was determined that the material eluted in the size range of about 100 to 200 kD, as opposed to the predicted 15 kD size. It was then discovered that the heating of the small aggregates resulted in a shift on HPLC profiles and also non-denaturing gels, to a species of approximately 20 to 40 kD, the expected range for the native folded material. The heating conditions employed were 80° C. for 20 minutes in buffered saline.

Although at present it is not possible to definitively state whether the refolded A33 D1 has adopted its native, biologically active conformation, it can be concluded from these data that the highly charged peptide extension promotes solubility of denatured proteins following removal of the denaturing agent. Thus, the charged peptide extensions may function by a similar mechanism to promote folding of proteins in vivo and in vitro. For in vitro refolding, extension of either terminus of the protein with highly-charged peptides should introduce a strong repulsive force that promotes solubility during both chemical and heat denaturation processes.

8. Production of a Synthetic T7A Peptide and Antibody Generation.

A synthetic peptide corresponding in sequence to peptide T7A was produced, as shown:

```
                                        (SEQ ID NO: 4)
        (acetyl-cysteine)-LEDPAANKARKEAELAAATAEQ.
```

An amino-terminal cysteine residue was incorporated into the peptide to introduce a reactive sulfhydryl group which could be utilized to couple the peptide to solid supports or carrier proteins.

In one set of experiments, the synthetic T7A peptide was added to in vitro protein refolding reactions to determine whether the peptide could improve yields of soluble protein in trans. Several different test protein systems were examined. In no case was the yield of soluble protein increased by addition of the synthetic peptide (data not shown). These data support a hypothesis that the peptide extensions act to confer self-chaperoning activity to the fusion protein and that the peptides act in cis, not in trans.

In another set of experiments, the peptide, covalently coupled to Sepharose beads, was used to investigate whether E. coli proteins with known chaperone activity in lysates of E. coli became bound to the immobilized peptide. Eluates of lysates passed over the peptide-Sepharose beads were analyzed by Western blotting, using monoclonal antibodies specific for several different E. coli chaperones. Eluates did not contain concentrations of chaperones that were detectable by this method, consistent with the studies described above, which indicated that the T7-derived peptide extensions do not function by recruiting trans-acting chaperones.

In a final set of experiments, the synthetic T7A peptide was conjugated to KLH (keyhole limpet hemocyanin) carrier protein, emulsified in complete Freund's adjuvant and injected subcutaneously into rabbits for production of antiserum. The resultant antiserum actively bound to all T7 peptides shown in Table 1, including the N1 through N7 peptides, but not to the T3 peptide.

Preparation of Peptide Extensions

DNA fragments encoding the peptide extensions of Table 1 were generated by PCR amplification of bacteriophage T7 genomic DNA or a subcloned region of the bacteriophage T3 DNA genome, using Pfu polymerase and primer sets to adapt fragment ends for ligation between the XhoI/BlpI or the BamHI/BlpI sites of pET15b. The amino acid sequence changes listed in Table 1 were introduced via mutagenic primers following established methods for PCR mutagenesis (Sarkar, et al. Biotechniques 8:404-407 (1990)). Peptides N1-N7 were amplified with primers adapting it for cloning between the NcoI/NdeI sites of pET15b to allow fusion of the peptide to the amino terminus of target proteins.

Thus, each of the peptide extension-encoding sequences could be readily incorporated into the basic pET15b vector to be used in the above experiments. Similar methods can be used to create other restriction sites at the ends of the peptide extension sequences and thus for introduction into other expression vectors and other locations within the vectors.

Sequences Encoding Peptide Extensions

The primers for PCR amplification of the sequences encoding the peptide extensions were designed to include restriction endonuclease sites for easy insertion of the sequences into the expression vector used for these studies. Each of the sequences was prepared from sequences in the T7 genome corresponding to the gene 10B segment of the capsid protein. The basic sequence from which each was derived is represented by SEQ ID NO: 43 and includes SEQ ID NOS: 44, 45 and 46 by way of example.

TABLE 1

| Peptide Name | Sequence | Net Charge[a] | SEQ ID NO: |
|---|---|---|---|
| T7C | LEDPFQSGVMLGVASTVAASPEEASVTSTEETLTPAQEAARTRAANKARKEAELAAATAEQ | −6 | 5 |
| T7B | LEDP----------------EEASVTSTEETLTPAQEAARTPAANKARKEAELAAATAEQ | −6 | 6 |
| T7B1 | LEDP----------------EEASVTSTEETLTPAQEAARTPAANKARKEAEL---TAEQ | −6 | 7 |
| T7B2 | LEDP----------------EEASVTSTEETLTPAQEAARTRPPNKARKEAELAAATAEQ | −6 | 8 |
| T7B3 | LEDP----------------EEASVTSTEETLTPAQEAARTRGGNKARKEAELAAATAEQ | −6 | 9 |
| T7B4 | LEDP----------------------------TPAQEAARTRAANKARKEAELAAATAEQ | −2 | 10 |
| T7B5 | LEDP----------------EEASVTSTEETLTPAQEAARTRAANKARKEAELEAETAEQ | −8 | 11 |
| T7B6 | LEDP----------------EEASVTSTEETLTPAQEAAETEAANKARKEAELEAETAEQ | −12 | 12 |
| T7B7 | LEDP----------------EEASVTSTEETLTPAQEAARTRAEEEAELEAETAEQ | −12 | 13 |
| T7B8 | LEDP----------------EEASVTSTEETLTPAQEAAETEAANKAEEEAELEAETAEQ | −16 | 14 |
| T7B9 | LEDP----------------EEASVTSTEETLTPAQEAARTRAANKARKEAELAA----- | −5 | 15 |
| T7B10 | LEDP----------------EEASVTSTEETLTPAQEAARTRAANKARKEAELAAA---- | −5 | 16 |
| T7B11 | LEDP----------------EEASVTSTEETLTPAQEAARTRAAAKARKEAELAAATAEQ | −6 | 17 |
| T7B12 | LEDP----------------EEASVTSTEETLTPAQEAARTR---KARKEAELAAATAEQ | −6 | 18 |
| T7B13 | LEDP----------------EEASVTSTEETLTPAQEAARTRAANK---EAELAAATAEQ | −8 | 19 |
| T7A | LEDP-----------------------------------AANKARKEAELAAATAEQ | −3 | 20 |
| T7A1 | LEDP-----------------------------------ERNKERKEAELAAATAEQ | −4 | 21 |
| T7A2 | LEDP-----------------------------------ERNKERKEAELEAATAEQ | −5 | 22 |
| T7A3 | LEDP-----------------------------------ERNKERKEAELEAETAEQ | −6 | 23 |
| T7A4 | LEDP-----------------------------------AANKARKEAELEAATAEQ | −4 | 24 |
| T7A5 | LEDP-----------------------------------AANKARKEAELEAETAEQ | −6 | 25 |
| T3 | LEDP----------------AVWEAGKVVAKGVGTADITATTSNGLIASCKVIVNAATS | −2 | 26 |
| N1 | ------------------M-EEASVTSTEETLTPAQEAARTRAANKARKEAELAAATAEH | −2 | 27 |
| N2 | ------------------MAERASVTSTEETLTPAQEAARTRAANKARKEAELAAATAEH | 0 | 28 |
| N3 | ------------------MAEEAKVTSTEETLTPAQEAARTPAANKARKEAELAAATAEH | +1 | 29 |
| N4 | ------------------MAERAKRTSTEETLTPAQEAARTRAANKARKEAELAAATAEH | +2 | 30 |
| N5 | ------------------M-EEASVTSTEETLTPAQEAARTRAANKARKEAELEAETAEH | −4 | 31 |
| N6 | ------------------M-EEASVTSTEETLTPAQEAAETEAANKARKEAELEAETAEH | −8 | 32 |
| N7 | ------------------M-EEASVTSTEETLTPAQEAARTRAANKAEEEAELEAETAEH | −8 | 33 |

[a] The terminal COO⁻ and NH₃⁺ groups of carboxyl-terminal and amino-terminal peptide extensions were included in the calculation of peptide net charge Sequences Encoding Peptide Extensions T7C, T7A1, T7A2 and T7A3

T7C:
SEQ ID NO: 47
CTCGAGGATCCGTTTCAAAGTGGAGTAATGCTGGGGGTGGCCTCAACGGTCGCTGCTAGTCCCGAAGAGGCGAGTGTTA
CTTCAACAGAAGAAACCTTAACGCCAGCACAGGAGGCCGCACGCACCCGCGCTGCTAACAAAGCCCGAAAGGAAGCTGA
GTTGGCTGCTGCCACCGCTGAGCAATAA

T7A1:
SEQ ID NO: 48
CTCGAGGATCCGGAACGCAACAAAGAGCGAAAGGAAGCTGAGTTGGCTGCTGCCACCGCTGAGCAATAA

T7A2:
SEQ ID NO: 49
CTCGAGGATCCGGAACGCAACAAAGAGCGAAAGGAAGCTGAGTTGGAGGCTGCCACCGCTGAGCAATAA

T7A3:
SEQ ID NO: 50
CTCGAGGATCCGGAACGCAACAAAGAGCGAAAGGAAGCTGAGTTGGAAGCTGAGACCGCTGAGCAATAA

TABLE 2

Effect of T7B carboxyl-terminal peptide extension on the folding of yeast proteins

| SwissProt Access # ([a]) | Protein size (# of amino acids) | Improvement 37° C. ([b]) | Improvement 25° C. ([b]) |
|---|---|---|---|
| P06633 (1) | 220 | 85% | 85% |
| P40099 (9) | 210 | none | none |
| P40961 (55) | 287 | none | none |
| P46948 (56) | 246 | none | 50% |
| P18562 (60) | 251 | none | 30% |
| P40530 (65) | 394 | none | none |
| P47076 (67) | 161 | 10% | 70% |
| P06838 (84) | 210 | none | none |
| Q03219 (90) | 274 | 50% | 50% |
| P53889 (96) | 259 | 50% | 70% |
| P53727 (99) | 317 | none | 10% |
| P06174 (106) | 275 | none | none |
| Q02784 (107) | 150 | 50% | 70% |

([a]) numbers in parentheses are ID numbers assigned to yeast proteins selected for analysis by the Brookhaven National Laboratory (BNL) Proteomics Project (see the Biology Department Web Site at the bnl.gov Web Site).

([b]) estimated increase in the recovery of protein in the soluble fraction of cell lysates, as compared to the yield of the unmodified protein expressed under similar conditions.

The invention claimed is:

1. A bacterial expression vector for expression of a recombinant protein or polypeptide of interest as a fusion product composed of said protein or polypeptide of interest fused at one terminus to a solubility enhancing peptide extension, said expression vector comprising a nucleic acid sequence encoding a solubility enhancing peptide extension selected from the group consisting of sequences SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 21, SEQ ID NO: 22, SEQ ID NO: 23, SEQ ID NO: 24, SEQ ID NO: 25, SEQ ID NO: 27, SEQ ID NO: 29, SEQ ID NO: 31, SEQ ID NO: 32, and SEQ ID NO: 33.

2. The vector of claim 1 wherein the one terminus of the protein or polypeptide of interest is the carboxyl terminus.

3. The vector of claim 1 wherein the one terminus of the protein or polypeptide of interest is the amino terminus.

4. The vector of claim 2 wherein the peptide extension is selected from the group consisting of sequences SEQ ID NO: 5, SEQ ID NO: 6, SEQ ID NO: 7, SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 21, SEQ ID NO: 22, SEQ ID NO: 23, SEQ ID NO: 24, and SEQ ID NO: 25.

* * * * *